United States Patent [19]

Sklavounos

[11] Patent Number: 4,465,626

[45] Date of Patent: Aug. 14, 1984

[54] PROCESS FOR PREPARATION, ISOLATION AND PURIFICATION OF DIPEPTIDE SWEETENERS

[75] Inventor: Constantine Sklavounos, Waterford, Conn.

[73] Assignee: Pfizer Inc., New York, N.Y.

[21] Appl. No.: 449,039

[22] Filed: Dec. 13, 1982

Related U.S. Application Data

[62] Division of Ser. No. 300,366, Sep. 8, 1981, Pat. No. 4,375,430.

[51] Int. Cl.$^3$ ............................................ C07C 103/52
[52] U.S. Cl. ............................................. 260/112.5 R
[58] Field of Search .................. 260/112.5 R; 424/177

[56] References Cited

U.S. PATENT DOCUMENTS

| | | | |
|---|---|---|---|
| 3,678,026 | 7/1972 | Ariyoshi et al. | 260/112.5 R |
| 3,808,190 | 4/1974 | Daflamans et al. | 260/112.5 R |
| 4,375,430 | 3/1983 | Sklavounos | 260/112.5 R |

FOREIGN PATENT DOCUMENTS

| | | |
|---|---|---|
| 34876 | 9/1981 | European Pat. Off. . |
| 8096557 | 10/1973 | Japan . |

OTHER PUBLICATIONS

Ariyoshi et al., Bull. Chem. Soc., Japan 46, pp. 1893–1895.

*Primary Examiner*—Delbert R. Phillips
*Assistant Examiner*—F. T. Moezie
*Attorney, Agent, or Firm*—Charles J. Knuth; Albert E. Frost; Robert K. Blackwood

[57] ABSTRACT

Aromatic sulfonic acid salts of certain dipeptide sweeteners which are L-aspartyl-D-alaninamides or L-aspartyl-D-serinamides, each substituted on amide nitrogen with an organic radical having a highly branched carbon skeleton; the process for preparing said salts by crystallization; and utilization of this crystallization process in processes for the preparation, isolation and purification of said amides.

25 Claims, No Drawings

PROCESS FOR PREPARATION, ISOLATION AND PURIFICATION OF DIPEPTIDE SWEETENERS

CROSS-REFERENCE TO RELATED APPLICATION

The present application is a division of copending application Ser. No. 300,366, filed Sept. 8, 1981, now U.S. Pat. No. 4,375,430.

BACKGROUND OF THE INVENTION

The present invention is concerned with processes for the preparation, isolation and purification of certain L-aspartyl-D-alaninamides and L-aspartyl-D-serinamides having a branched organic radical as substituent on the amide nitrogen. These processes in all instances include crystallization of said amides as acid addition salts with aromatic sulfonic acids. These salts per se, in anhydrous or hydrated form, are also encompassed by the present invention.

The aforementioned amides are potent synthetic sweeteners. The D-alaninamide derivatives are fully disclosed as to preparation and utility in European Patent Document No. 34,876, published Sept. 2, 1981. The D-serinamide derivatives, prepared and tested by the same methods, are described in copending U.S. patent application, Ser. No. 276,243, filed June 26, 1981, for "Branched Amides of L-Aspartyl-D-Amino Acid Dipeptides" to Brennan and Hendrick. While both of these patent documents refer in general to pharmaceutically-acceptable acid addition salts, there is no mention of sulfonic acid salts.

In both the D-alanine and D-serine series, two of the earlier preferred methods of synthesis involve multistep sequences, generally requiring protection and subsequent deprotection of amine and/or carboxyl groups. The present crystallization process offers an advantageous method for purification of said dipeptide sweeteners when prepared by one of these earlier preferred methods.

A more particular and surprising advantage of the present invention is in the "one-step" synthesis presented earlier as a third preferred method in both the D-alanine and D-serine series. In this latter process L-aspartic N-thiocarboxyanhydride is reacted with a suitably subsituted D-alaninamide or D-serinamide to yield the desired dipeptide amide directly. Disadvantages of the latter process are the tendency to coproduce isomeric D-aspartyl-D-amino acid amide and tripeptide (L-aspartyl-L-aspartyl-D-amino acid amide), as well as traces of foul smelling sulfur compounds generally difficult to remove (cf. Vinick, U.S. Pat. No. 4,238,392, December 1980, whereby alkali metal periodates are employed to deodorize L-aspartyl-L-phenylalanine alkyl esters prepared by use of L-aspartic acid N-thiocarboxyanhydride). Surprisingly, the present crystallization process urges out the tripeptide and the diastereomeric D-aspartyl-D-amino acid amide (even when the latter is present in high concentration, e.g. 10%). Furthermore, odiferous sulfur compounds are reduced in level or eliminated. Thus the present invention renders an earlier "third preferred process" now a particularly preferred process.

The present invention also encompasses another, particularly preferred, "one-step" process which is novel to the synthesis of the present compounds. An acid addition salt of L-aspartic acid anhydride is coupled with the same suitably substituted D-alaninamide or D-serinamide. In this process there is no odor problem such as that noted above; however, a large amount (generally an amount equal to about one-half that of the desired product) of the beta-L-aspartyl isomer is formed in this process, as well as some tripeptide (L-aspartyl-L-aspartyl-D-alaninamide or -serinamide). Surprisingly both the beta-isomer and the tripeptide are removed by the present crystallization process.

Ariyoshi et al. [Bull. Chem. Soc. Japan, 46, pp. 1893–1895 (1975)] have described the preparation of aspartame (L-aspartyl-L-phenylalanine methyl ester) from L-aspartic acid anhydride hydrochloride and methyl L-phenylalanate hydrochloride. Partial purification was achieved by crystallization of hydrochloride salt, but column chromatography was employed for the ultimate purification of the desired product, not the selective crystallization of the present invention, which as noted below, is not applicable to aspartame.

Although certain aromatic carboxylic acid salts have been used to separate aspartame from its beta-L-aspartyl isomer (Ariyoshi and Sato, U.S. Pat. No. 3,673,026, July 1972), the present result is all the more suprising in view of the facts that (1) aspartame does not crystallize from water in the presence of p-toluenesulfonic acid, i.e. under the present conditions; and (2) the aromatic carboxylic acid salts of Ariyoshi and Sato are not operative with the present dipeptide amide sweeteners.

SUMMARY OF THE INVENTION

The present invention is concerned with a process for the isolation and purification of an L-aspartyl-D-amino acid dipeptide amide of the formula

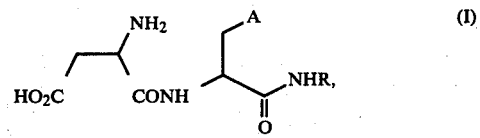

wherein A is hydrogen or hydroxy and R is

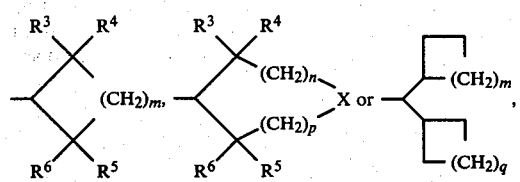

wherein at least one of $R^3$, $R^4$, $R^5$ and $R^6$ is $(C_1$–$C_4)$alkyl and the remainder are hydrogen or $(C_1$–$C_4)$alkyl; X is O, S, SO, $SO_2$, C=O or CHOH; m is zero, 1, 2, 3 or 4; and n, p and q are each zero, 1, 2 or 3; with the provisos that the sum of n+p is not greater than 3, the sum of the carbon atoms in $R^3$, $R^4$, $R^5$ and $R^6$ is not greater than six, and when both of $R^3$ and $R^4$ or $R^5$ and $R^6$ are alkyl they are methyl or ethyl;

which comprises selectively crystallizing said L-aspartyl-D-amino acid dipeptide amide in the form of a salt with an aromatic sulfonic acid of the formula

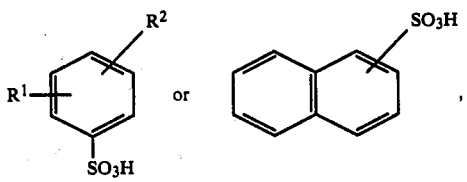

wherein $R^1$ is hydrogen, chloro or methyl and $R^2$ is hydrogen or methyl, from an aqueous solvent. The resulting salt is generally hydrated. When the anhydrous salt is desired, the water of hydration is removed by heating in vacuo over phosphorus pentoxide.

The present invention also encompasses the resulting substantially pure, anhydrous or hydrated salt, which comprises an L-aspartyl-D-amino acid dipeptide amide of the formula (I) and an aromatic sulfonic acid as defined above.

Thirdly, the present invention encompasses an improved process for the preparation of purified L-aspartyl-D-amino acid dipeptide amides of the formula (I), in the form of an acid addition salt with an aromatic sulfonic acid as defined above, which comprises:

(a) reacting L-aspartyl N-thiocarboxy anhydride of the formula

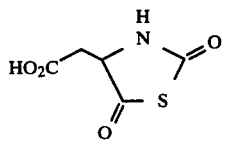

with D-amino acid amide of the formula

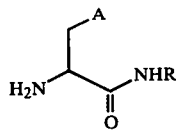

(II)

wherein A and R are as previously defined, in an aqueous solvent at a basic pH; and, after acidification to effect standard dethiocarboxylation of the resulting intermediate;

(b) crystallizing the resulting L-aspartyl-D-amino acid dipeptide with said aromatic sulfonic acid.

Finally, the present invention encompasses a novel process for the preparation of compounds of the formula (I) in the form of a purified acid addition salt with an aromatic sulfonic acid as defined above, which comprises:

(a) reacting an acid addition salt of L-aspartic acid anhydride of the formula

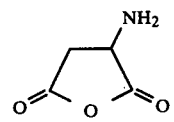

with a D-amino acid amide of the formula (II) in a reaction inert solvent; and, after standard quench and transfer of the product into water;

(b) crystallizing the resulting L-aspartyl-D-amino acid dipeptide with said sulfonic acid.

The expression "acid addition salt" as applied to L-aspartic acid anhydride refers generally to strong acids, such as hydrochloric acid, which stabilize the anhydride and prevent its polymerization.

The expression "reaction-inert solvent" is intended to encompass those solvents which do not react with starting materials or product in a manner which significantly reduces the yield of desired product. Exemplary solvents which meet this criteria are detailed hereinafter.

Exemplary of the aromatic sulfonic acids structurally defined above are benzenesulfonic acid, p-toluenesulfonic acid, p-chlorobenzenesulfonic acid, 3,4-xylenesulfonic acid, 2,5-xylenesulfonic acid, alpha-napthalenesulfonic acid and beta-naphthalenesulfonic acid.

When R is

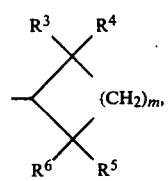

the preferred embodiments of the present invention have m as 2 and $R^3$, $R^4$, $R^5$ and $R^6$ as methyl, or m as 3, $R^3$ and $R^6$ as hydrogen and $R^4$ and $R^5$ as methyl, without particular preference in regard to the value of A, or the aromatic sulfonic acid.

When R is

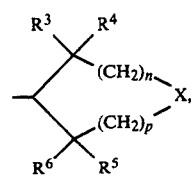

the preferred values of n and p are 0, with $R^3$, $R^4$, $R^5$ and $R^6$ are as methyl. Within this subgenus more preferred compounds have X as S, SO or $SO_2$. Furthermore, when X is S and A is hydrogen, the most preferred salts are with p-toluenesulfonic acid, beta-naphthalenesulfonic acid, alpha-naphthalenesulfonic acid or benzenesulfonic acid; and when X is $SO_2$ and A is hydrogen, or when X is S and A is hydroxy, the most preferred salt is with p-toluenesulfonic acid.

Finally when R is

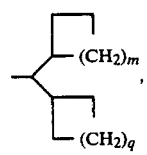

the preferred value of both m and q is 0. Within this subgenus, the more preferred value of A is hydrogen. The most preferred salts are with p-chlorobenzenesulfonic acid, 3,4-dimethylbenzenesulfonic acid, alpha-naphthalenesulfonic acid or beta-naphthalenesulfonic acid.

These preferences are based on the particularly high sweetness of the resulting dipeptide, as well as on the fact that the processes for their crystallization are particularly facile, readily producing crystalline products of analytical purity.

DETAILED DESCRIPTION OF THE INVENTION

The process of the present invention is readily carried out. An aqueous solution, containing an L-aspartyl-D-amino acid dipeptide amide of the formula (I), is treated, portionwise, with at least one molar equivalent of an aromatic sulfonic acid, as defined above, usually with vigorous stirring. Yields are generally improved by use of an excess of the sulfonic acid (preferably less that two equivalents), higher concentrations of said crude compound (preferably in the range of about 5-10% w/v), but not so high as to cause co-precipitation of impurities; and cooling, preferably to the range of about 0°-25° C. Purity is generally improved by slow crystallization (slow addition of acid, slow cooling) and digestion (i.e. stirring for up to several hours after initial crystallization is complete). It is preferred that the solvent be substantially aqueous, but the presence of small amounts of organic solvents in solution present no significant disadvantage.

Crude L-aspartyl-D-amino acid dipeptide amides of the formula (I) are prepared according to methods disclosed in the European patent document noted above, which is specifically concerned with the D-alaninamide derivatives. The same methods are used for the D-serinamide analogs, substituting appropriate D-serine derivatives for the D-alanine derivatives of the European patent document, as detailed in the above noted co-pending U.S. patent application. Crude dipeptide amides prepared by one of these processes are dissolved in water at a level of about 5-20% and clarified by filtration if necessary for use in the present crystallization process. Alternatively, after the deprotection step, the dipeptide amide is crystallized directly from an aqueous stream, without prior isolation of the crude product.

One of the particularly preferred overall processes for compounds of the formula (I), as embodied by the present invention, represents a distinct improvement in one of the processes disclosed in the above European patent document and copending U.S. application. A D-amino acid amide of the formula (II) is reacted with L-aspartic acid N-thiocarboxyanhydride to provide directly the compounds of formula (I). In carrying out this method the amide (II) in a suitable solvent is contacted with an equimolar amount of L-aspartic acid N-thiocarboxyanhydride at a mildly alkaline pH at a temperature of from about −25° to 10° C. to provide the compound of formula (I). The alkaline pH for this reaction is provided by means of a strong base, for example, sodium hydroxide or potassium carbonate. Suitable solvents for this reaction are those that dissolve at least a portion of the reactants under the reaction conditions employed without reacting with either reactant to an appreciable extent and allow the products formed in the reaction to be isolated with relative ease. Examples are water, tetrahydrofuran, 1,1-dimethoxyethane, or mixtures thereof. In the present instance the preferred solvent is water. The latter not only avoids the expense of an organic solvent, but is the solvent which provides simple, straight-forward isolation of the product; if it is desired to operate at a temperature much below 0° C., the preferred diluent is tetrahydrofuran. A preferred alkaline pH range for this reaction is from about 8 to 10 and a pH of about 9 is especially preferred. An especially preferred temperature is in the range of about −2° to 5° C.; generally producing clean product and obviating the need for an organic solvent.

Under the preferred conditions mentioned above the reaction is ordinarily complete in one or two hours. The product of formula (I) is then isolated by adjusting the pH to the slightly acid side (which effects dethiocarboxylation of the intermediate

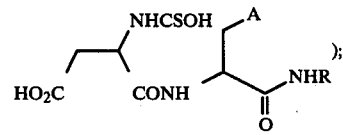

removing or displacing organic solvents, if present, with water; and adding the appropriate aromatic sulfonic acid. If desired, acidification is accomplished with the same sulfonic acid used to crystallize the product. The addition of sulfonic acid is usually done in portions, with optional cooling or concentration as necessary to induce crystallization of the desired product. The crystalline salt is recovered in the normal fashion by filtration or centrifugation, usually after chilling and digesting the mixture for a time period ranging from a few minutes up to 24 hours, or more, if desired.

A second particularly preferred, overall process, which in this case is novel at all stages, involves reaction of the same D-amino acid amide of the formula (II) with an acid addition salt of L-aspartic acid anhydride. Again, compounds of the formula (I) are provided directly. The reaction is preferably carried out using an excess of the amide, which is recovered by extraction and recycled. The reaction is carried out at low temperature, e.g. −40° C. to 0° C., preferably about −15° C. to −25° C. in a water-immiscible, reaction-inert solvent such as methylene chloride or ethylene chloride in the presence of a small amount of a weak acid such as acetic acid and, if desired, in the presence of a small amount of a lower alkanol such as methanol. After reaction is complete (about 0.5 hour at −20° C.), the reaction is quenched into water and the pH adjusted to the basic side (e.g. 9 to 11.5). Starting amide is recovered from the organic layer and extracts of the aqueous layer. The aqueous layer is then acidified with a strong mineral acid and the desired L-aspartyl-D-amino acid dipeptide amide recovered as an aromatic sulfonate salt by addition of at least one equivalent of the sulfonic acid under conditions described above. The undesired beta-isomer (generally present at about half the concentration of the desired isomer) and other contaminants, particularly tripeptide (L-aspartyl-L-aspartyl-D-amino acid amide) remain in solution.

The amides of the formula (II) used as starting materials are prepared according to methods detailed in the above referenced European patent document, which specifically describes alanine analogs. The above-mentioned U.S. patent application identically discloses preparation of the serine analogs, except that the hydroxymethyl group of D-serine of course replaces the methyl group of D-alanine.

The free L-aspartyl-D-amino acid dipeptide amides of the formula (I) are readily regenerated from the present aromatic sulfonate salts by standard methods of neutralization and extraction, or preferably by neutralization with a basic ion exchange resin which takes up the sulfonic acid. If desired, the free base need not be isolated, but can be converted "in situ" to a pharmaceutically-acceptable acid addition or cationic salt, and then isolated as the salt.

When an exchange resin is employed to convert the aromatic sulfonate salt to free base, a weakly basic ion exchange resin is preferred. Most preferred is a weakly basic liquid anion exchange resin such as Amberlite LA-1, which is a mixture of secondary amines wherein each secondary amine has the formula

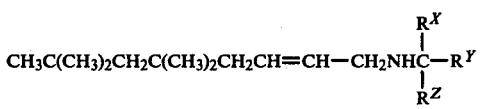

wherein each of $R^X$, $R^Y$ and $R^Z$ is an aliphatic hydrocarbon radical and wherein $R^X$, $R^Y$ and $R^Z$ contain in the aggregate from 11 to 14 carbon atoms; this particular mixture of secondary amines which is sometimes referred to as "Liquid Amine Mixture No. I," is a clear amber liquid having the following physical characteristics: viscosity at 25° C. of 70 cps.; specific gravity at 20° C. of 0.845; refractive index at 25° C. of 1.467; distillation range at 10 mm.: up to 160° C.—4%, 160° to 210° C.—5%, 210° to 220° C.—74%, above 220° C.—17%.

The sweetness potency of these compounds is determined by methods described in the above referenced European patent document, as are methods for their use as sweetening agents.

The present invention is illustrated by the following Examples. However, it should be understood that the invention is not limited to the specific details of these Examples.

The HPLC (high performance liquid chromatography) method referred to in these Examples employed a 3.9 mm.×30 cm., micro-Bondapak $C_{18}$ column (Waters Associates, Inc., Milford, Mass. 01757). The mobile phase was 9:1 0.02M ammonium acetate adjusted to pH 4.8 with acetic acid:acetonitrile; the flow rate was 2 ml./minute; the detector was ultraviolet, 220 nm.

EXAMPLE 1

3-(L-Aspartyl-D-alaninamido)-2,2,4,4-tetramethylthietane p-Toluenesulfonate 3-(D-alaninamido)-2,2,4,4-tetramethylthietane (300 g., 1.39 mole) was dissolved in water (2.5 liter) at 0°-5° C. and the pH of the solution adjusted to 9.0 with 12N hydrochloric acid. L-Aspartic acid N-thiocarboxyanhydride (292.2 g., 1.62 mole) was then added in portions with vigorous stirring; the pH was maintained at 8.5-9.5 by the addition of 50% sodium hydroxide solution as needed. Stirring and addition of hydroxide was continued while the pH stabilized at 9.0 (ca. 90 minutes). The pH was then adjusted to 5.0-5.5 with 12N hydrochloric acid. The reaction mixture was analyzed by HPLC and found to contain the free base of title product in 90% yield (retention time: 15 minutes) contaminated with about 5% 3-(D-aspartyl-D-alaninamido)-2,2,4,4-tetramethylthietane (retention time: 12.9 minutes) and about 5% 3-(L-aspartyl-L-aspartyl-D-alaninamido)-2,2,4,4-tetramethylthietane (retention time: 8.7 minutes). p-Toluenesulfonic acid monohydrate (285.3 g., 1.5 mole) was then added in portions over a period of one hour. The precipitated crystalline title product as a monohydrate was collected by filtration, washed with a small quantity of water, and dried. The isolated yield of pure product was 567 g. (78.2%); m.p. 182–6.

Anal. Calcd. for $C_{21}H_{33}O_7N_3S_2.H_2O$: C, 48.35; H, 6.76; N, 8.05; $H_2O$, 3.45. Found: C, 47.55; H, 6.48; N, 7.98; $H_2O$, 3.99.

Substituting an equivalent quantity of the appropriate amide for 3-(D-alaninamido)-2,2,4,4-tetramethylthietane, the same process is employed to produce the following products:

3-(L-aspartyl-D-alaninamido)-2,2,4,4-tetramethylthietane 1-oxide p-toluenesulfonate;

3-(L-aspartyl-D-alaninamido)-2-methyltetrahydrothiophene p-toluenesulfonate;

3-(L-aspartyl-D-alaninamido)-2,2,4,4-tetramethyloxetane p-toluenesulfonate;

4-(L-aspartyl-D-alaninamido)-3-methylcyclohexanone p-toluenesulfonate;

2-(L-aspartyl-D-alaninamido)-1,1,3,3-tetramethylcyclopentane p-toluenesulfonate;

2-(L-aspartyl-D-alaninamido)-1,3-dimethylcyclohexane p-toluenesulfonate;

1-(L-aspartyl-D-alaninamido)-2-ethylcyclohexane p-toluenesulfonate;

1-(L-aspartyl-D-alaninamido)-1,1-dicyclopropylmethane p-toluenesulfonate; and 1-(L-aspartyl-D-alaninamido)-1-cyclobutyl-1-cyclopentylmethane p-toluenesulfonate.

When a 10% water solution of 3-(D-aspartyl-D-alaninamido)-2,2,4,4-tetramethylthietane was treated with an equivalent of p-toluenesulfonic acid monohydrate, the solution remained clear, even when refrigerated for 2 days. Thus the title salt is separated from this isomer by crystallization from water according to the procedure of the present Example, even if present in high concentration.

If desired, the hydrate form of the title salt is converted to the anhydrous form by heating at 80° in high vacuum over phosphorus pentoxide until dehydration is essentially complete (conveniently about 16 hours). The other salts of this Example produced in hydrated form are, if desired, made anhydrous in the same manner.

EXAMPLE 2

3-(L-Aspartyl-D-alaninamido)-2,2,4,4-tetramethylthietane beta-Naphthalenesulfonate Following the procedure of Example 1, but using beta-naphthalenesulfonic acid instead of p-toluenesulfonic acid, crystalline title product (as monohydrate) was obtained in 71.8% yield; m.p. 178–180.

Anal. Calcd. for $C_{24}H_{33}N_3O_7S_2.H_2O$: C, 51.69; H, 6.33; N, 7.53; $H_2O$, 3.23. Found: C, 50.83; H, 6.06; N, 7.07; $H_2O$, 3.52.

Substituting the appropriate aromatic sulfonic acid for p-toluenesulfonic acid of Example 1, the following additional salts are obtained:

3-(L-aspartyl-D-alaninamido)-2,2,4,4-tetramethylthietane 3,4-xylenesulfonate;

3-(L-aspartyl-D-alaninamido)-2,2,4,4-tetramethylthietane 2,5-xylenesulfonate;

3-(L-aspartyl-D-alaninamido)-2,2,4,4-tetramethylthietane p-chlorobenzenesulfonate.

EXAMPLE 3

3-(L-Aspartyl-D-alaninamido)-2,2,4,4-tetramethylthietane alpha-Naphthalenesulfonate Following the procedure of Example 1, but using alpha-naphthalenesulfonic acid instead of p-toluenesulfonic acid, crystalline title product was obtained in 50% yield; m.p. 200–1.

Anal. Calcd. for $C_{24}H_{33}N_3O_7S_2$: C, 53.41; H, 6.16; N, 7.79. Found: C, 52.95; H, 6.16; N, 7.61.

EXAMPLE 4

3-(L-Aspartyl-D-alaninamido)-2,2,4,4-tetramethylthietane Benzenesulfonate

Benzenesulfonic acid monohydrate (2.64 g., 15 mmoles) was added over 30 minutes in portions with vigorous stirring to 50 ml. of a water solution containing 4.75 g. of the free base form of title product. The mixture was stirred for an additional three hours. The separated crystals of title product (as a monohydrate) were collected by filtration, washed with a small quantity of water, and dried. The yield was 4.5 g. (65%); m.p. 185-8.

Anal. Calcd. for $C_{20}H_{31}N_3O_7S_2.H_2O$: C, 47.32; H, 6.16; N, 8.28; $H_2O$, 3.55. Found: C, 47.51; H, 6.51; N, 8.31, $H_2O$, 3.70.

EXAMPLE 5

Regeneration of 3-(L-Aspartyl-D-alaninamido)-2,2,4,4-tetramethylthietane from the p-Toluenesulfonate Salt A mixture of Amberlite LA-1 (liquid anion exchange resin; 49.2 ml.), methylene chloride (73.8 ml.), deionized water (115 ml.), and the title salt of Example 1 (monohydrate; 23 g., 44 mmole) was stirred for one hour, resulting in two clear layers. The aqueous layer was treated with carbon, clarified by filtration, concentrated to about 32 ml., and cooled to 0°-5° C. to crystallize title product. The crystals were collected by filtration and dried. The isolated yield of pure product was 11.3 g. (70%).

The same procedure is used to regenerate corresponding free base from other salts of Examples 1-4.

EXAMPLE 6

3-(L-Aspartyl-D-alaninamido)-2,2,4,4-tetramethylthietane p-Toluenesulfonate 3-(D-Alaninamido)-2,2,4,4-tetramethylthietane (2.25 g., 10.4 mmole) was dissolved in methylene chloride (20 ml.); glacial acetic acid (0.24 g.) and methanol (0.21 ml.) were added. The mixture was cooled to −20° C. and L-aspartic acid anhydride hydrochloride [Ariyoshi et al., Bull. Chem. Soc. Japan, 45, pp. 2208-2209 (1973); 0.4 g., 2.6 mmole], was added with vigorous stirring. After stirring at −20° C. for 30 minutes the mixture was quenched with water (10 ml.), the pH was adjusted at 11.0 by the addition of 50% sodium hydroxide solution, and the layers were separated. The aqueous layer was extracted with methylene chloride (10 ml.) to remove unreacted amide. The solution was analyzed by HPLC and found to contain title product (retention time, 15 minutes), and the beta-L-aspartyl isomer (retention time, 14.4 minutes) in 70:30 ratio. After adjusting the pH of the solution at 6.0 with 12N hydrochloric acid, p-toluenesulfonic acid monohydrate (0.5 g., 3.6 mmole) was added in portions and the mixture was stirred for three hours. The separated crystalline mafterial (collected by filtration, washed with a small amount of water, and dried) has properties identical with those of material prepared according to Example 1. HPLC analysis showed this product be be free of the beta-isomer.

The appropriate amide is substituted for 3-(D-alaninamido)-2,2,4,4-tetramethylthietane to produce the following compounds:

3-(L-aspartyl-D-alaninamido)-2,2,4,4-tetramethylthietane 1-oxide p-toluenesulfonate;

3-(L-aspartyl-D-alaninamido)-2,2,4,4-tetramethylthietane 1,1-dioxide p-toluenesulfonate;

2-(L-aspartyl-D-alaninamido)-1,1,3,3-tetramethylcyclopentane p-toluenesulfonate;

2-(L-aspartyl-D-alaninamido)-1,3-dimethycyclohexane p-toluenesulfonate;

1-(L-aspartyl-D-alaninamido)-1,1-dicyclopropylmethane p-toluenesulfonate;

3-(L-aspartyl-D-serinamido)-2,2,4,4-tetramethylthietane p-toluenesulfonate;

1-(L-aspartyl-D-serinamido)-1,1-dicyclopropylmethane p-toluenesulfonate;

2-(L-aspartyl-D-serinamido)-1,1,3,3-tetramethylcyclohexane p-toluenesulfonate; and 2-(L-aspartyl-D-serinamido)-1,3-dimethylcyclohexane.

EXAMPLE 7

1-(L-Aspartyl-D-alaninamido)-1,1-dicyclopropylmethane p-Chlorobenzenesulfonate p-Chlorobenzenesulfonic acid (1.92 g., 10 mmole) was added portionwise and with vigorous stirring to a solution of crude free base form of title product (3.15 g., 10 mmole) in about 300 ml. water. The mixture was treated with carbon for 30 minutes, clarified by filtration, concentrated to a small volume (~40 ml.), and placed in a refrigerator for 16 hours. The separated crystalline title product as a monohydrate was collected by filtration, washed with a small amount of ice water and dried. The yield was 1.6 g. (32.6%); m.p. 146°-9° C.

Anal. Calcd. for $C_{20}H_{28}O_7N_3SCl.H_2O$: C, 47.29; H, 5.95; N, 8.27; $H_2O$, 3.54. Found: C, 47.30; H, 5.79; N, 8.41; $H_2O$, 3.59.

EXAMPLE 8

1-(L-Aspartyl-D-alaninamido)-1,1-dicyclopropylmethane 3,4-Xylenesulfonate

Following the procedure of Example 7, but using 3,4-xylenesulfonic acid instead of p-chlorobenzenesulfonic acid, crystalline title product as a hemihydrate was obtained in 14% yield.; m.p. 184-9.

Anal. Calcd. for $C_{22}H_{33}O_7N_3S.0.5\ H_2O$: C, 53.64; H, 6.96; N, 8.53; $H_2O$, 1.83. Found: C, 53.66; H, 7.01; N, 8.88; $H_2O$, 1.86.

EXAMPLE 9

1-(L-Aspartyl-D-alaninamido)-1,1-dicyclopropylmethane alpha-Naphthalenesulfonate Following the procedure of Example 7, but using alpha-naphthalenesulfonic acid instead of p-chlorobenzenesulfonic acid, crystalline title product was obtained in 65% yield; m.p. 195-8.

Anal. Calcd. for $C_{24}H_{31}N_3O_7S$: C, 57.01; H, 6.18; N, 8.31; $H_2O$, 0.00. Found: C, 56.44; H, 6.06; N, 8.40; $H_2O$, 0.73.

Free base form of title product (3.0 g.) contaminated with 10% of isomeric 1-(D-aspartyl-D-alaninamido)-1,1-dicyclopropylmethane was dissolved in 100 ml. of water. alpha-Naphthalenesulfonic acid (2.3 g.) was added portionwise over 1 hour with vigorous stirring. The resulting solution was refrigerated for 16 hours and the crystalline product recovered by filtration with small water wash and dried. HPLC analysis showed this title product to be free of the contaminating isomer (retention time of title product was 8.3 minutes; retention time for the diastereoisomer was 6.1 minutes).

EXAMPLE 10

1-(L-Aspartyl-D-alaninamido)-1,1-dicyclopropylmethane beta-Naphthalenesulfonate

Following the procedure of Example 7, but using beta-naphthalenesulfonic acid instead of p-chlorobenzenesulfonic acid, crystalline title product as a monohydrate was obtained in 52% yield; m.p. 167–170.

Anal. Calcd. for $C_{24}H_{31}N_3O_7S \cdot H_2O$: C, 55.05; H, 6.35; N, 8.04; $H_2O$, 3.44. Found: C, 54.92; H, 6.16; N, 8.09; $H_2O$, 3.45.

EXAMPLE 11

3-(L-Aspartyl-D-serinamido)-2,2,4,4-tetramethylthietane p-Toluenesulfonate

Following the procedure of Example 1, but using 3-(D-serinamido)-2,2,4,4-tetramethylthietane instead of 3-(D-alaninamido)-2,2,4,4-tetramethylthietane, title product as a hemihydrate was obtained in 78.3% yield; m.p. 208°–210° C.

Anal. Calcd. for $C_{21}H_{33}O_8N_3S_2 \cdot 0.5\ H_2O$: C, 47.71; H, 6.48; N, 7.95; $H_2O$, 1.70. Found: C, 47.48; H, 6.46; N, 8.21; $H_2O$, 1.70.

By the same procedure, substituting the appropriate amide of 3-(D-serinamido)-2,2,4,4-tetramethylthietane, the following compounds are prepared:

3-(L-aspartyl-D-serinamido)-2,2,4,4-tetramethylthietane 1,1-dioxide p-toluenesulfonate;

3-(L-aspartyl-D-serinamido)-2,2,4,4-tetramethylthietane 1-oxide p-toluenesulfonate;

4-(L-aspartyl-D-serinamido)-3,5-dimethylcyclohexanone p-toluenesulfonate;

2-(L-aspartyl-D-serinamido)-1,1,3,3-tetramethylcyclopentane p-toluenesulfonate;

2-(L-aspartyl-D-serinamido)-1,3-dimethylcyclohexane p-toluenesulfonate;

1-(L-aspartyl-D-serinamido)-2-ethylcycloheptane p-toluenesulfonate;

1-(L-aspartyl-D-serinamido)-1,1-dicyclopropylmethane; and 1-(L-aspartyl-D-serinamido-1,1-dicyclohexylmethane.

EXAMPLE 12

3-(L-Aspartyl-D-alaninamido)-2,2,4,4-tetramethylthietane 1,1-Dioxide p-Toluenesulfonate p-Toluenesulfonic acid monohydrate (2.1 g., 11 mmoles) was added in portions with vigorous stirring to a solution containing the free base form of title product (4.0 g., 10 mmoles) in 10 ml. water at 50° C. The mixture was then allowed to gradually cool to room temperature. Crystallization of title product as a monohydrate commenced within a few minutes. The mixture was cooled to 0° C. and stirred for about 10 hours to complete the crystallization. The product was collected by filtration, washed with a small quantity of ice water, and dried. The yield was 3.21 g. (58%); m.p. 166–9.

Anal. Calcd. for $C_{21}H_{33}O_9N_3S_2 \cdot H_2O$: C, 45.56; H, 6.37; N, 7.59; $H_2O$, 3.25. Found: C, 45.60; H, 6.15; N, 7.84; $H_2O$; 3.07.

Following the procedure of Example 1, but using 3-(D-alaninamido)-2,2,4,4-tetramethylthietane 1,1-dioxide instead of 3-(D-alaninamido)-2,2,4,4-tetramethylthietane, identical crystalline title product was obtained in 29.3% yield.

I claim:

1. A process for the preparation of an L-aspartyl-D-amino acid dipeptide amide of the formula

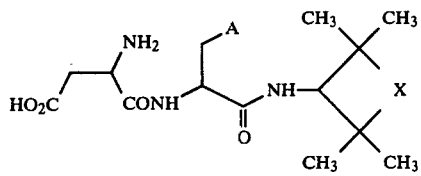

wherein A is hydrogen or hydroxy and X is S, SO or $SO_2$, in the form of an acid addition salt with an aromatic sulfonic acid of the formula

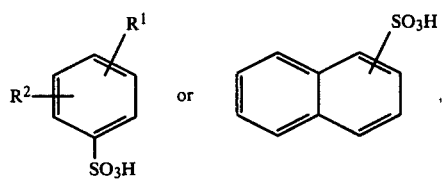

wherein $R^1$ is hydrogen, methyl or chloro and $R^2$ is hydrogen or methyl; which comprises (a) reacting an acid addition salt of L-aspartic acid anhydride of the formula

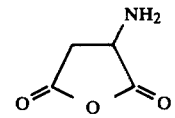

with a D-amino acid amide of the formula

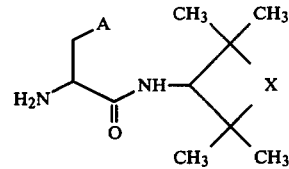

wherein A and X are as previously defined; and (b) crystallizing the resulting L-aspartyl-D-amino acid dipeptide with said sulfonic acid.

2. A process of claim 1 wherein the acid addition salt of the L-aspartic anhydride is the hydrochloride salt.

3. A process of claim 2 wherein X is $SO_2$.

4. A process of claim 3 wherein A is hydrogen and the aromatic sulfonic acid is p-toluenesulfonic acid.

5. A process of claim 2 wherein X is SO.

6. A process of claim 2 wherein X is S.

7. A process of claim 6 wherein A is hydrogen.

8. The process of claim 7 wherein the aromatic sulfonic acid is p-toluenesulfonic acid.

9. The process of claim 7 wherein the aromatic sulfonic acid is beta-naphthalene sulfonic acid.

10. The process of claim 7 wherein the aromatic sulfonic acid is alpha-naphthalene sulfonic acid.

11. The process of claim 7 wherein the aromatic sulfonic acid is benzenesulfonic acid.

12. A process of claim 6 wherein A is hydroxy.

13. The process of claim 12 wherein the aromatic sulfonic acid is p-toluenesulfonic acid.

14. A process for the preparation of an L-aspartyl-D-amino acid dipeptide amide of the formula

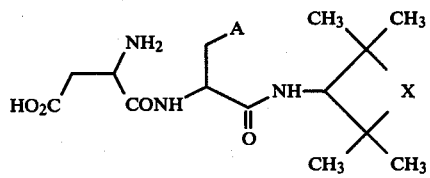

wherein A is hydrogen or hydroxy and X is S, SO or SO₂, in the form of an acid addition salt with an aromatic sulfonic acid of the formula

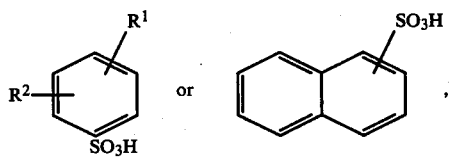

wherein R¹ is hydrogen, methyl or chloro and R² is hydrogen or methyl; which comprises (a) reacting L-aspartyl N-thiocarboxy anhydride of the formula

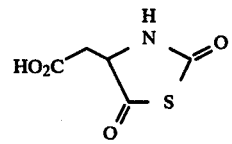

with a D-amino acid amide of the formula

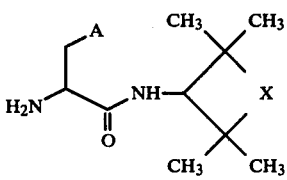

wherein A and X are as previously defined; in an aqueous solvent at a basic pH; and (b) crystallizing the resulting L-aspartyl-D-amino acid dipeptide with said aromatic sulfonic acid.

15. A process of claim 14 wherein X is SO₂.

16. A process of claim 15 wherein A is hydrogen and the aromatic sulfonic acid is p-toluenesulfonic acid.

17. A process of claim 14 wherein X is SO.

18. A process of claim 14 wherein X is S.

19. A process of claim 18 wherein A is hydrogen.

20. The process of claim 19 wherein the aromatic sulfonic acid is p-toluenesulfonic acid.

21. The process of claim 19 wherein the aromatic sulfonic acid is beta-naphthalene sulfonic acid.

22. The process of claim 19 wherein the aromatic sulfonic acid is alpha-naphthalene sulfonic acid.

23. The process of claim 19 wherein the aromatic sulfonic acid is benzenesulfonic acid.

24. A process of claim 18 wherein A is hydroxy.

25. The process of claim 24 wherein the aromatic sulfonic acid is p-toluenesulfonic acid.

* * * * *